United States Patent [19]

Clark, III

[11] 4,048,064

[45] Sept. 13, 1977

[54] BIOCOMPATIBLE HEMOPERFUSION SYSTEM

[76] Inventor: William T. Clark, III, Number Six Davis Blvd., New Orleans, La. 70121

[21] Appl. No.: 679,853

[22] Filed: Apr. 23, 1976

[51] Int. Cl.$^2$ .......................... A61K 23/02; B01D 3/00
[52] U.S. Cl. .............................. 210/23 R; 128/214 R; 210/22 A; 210/24; 210/282; 210/500 M; 210/DIG. 23; 424/183
[58] Field of Search ........... 210/22, 24 R, 282, 321 B, 210/446, 23 R, 500 M; 23/230 B; 128/214 R, DIG. 5, DIG. 22; 424/183

[56] References Cited

U.S. PATENT DOCUMENTS

| | | | |
|---|---|---|---|
| 2,214,925 | 9/1940 | Gutrie | 210/282 X |
| 3,522,346 | 7/1970 | Chang | 210/22 X |
| 3,617,344 | 11/1971 | Leininger et al. | 424/183 X |
| 3,634,123 | 1/1972 | Eriksson et al. | 424/183 X |
| 3,673,612 | 7/1972 | Merrill et al. | 210/22 X |
| 3,725,113 | 4/1973 | Chang | 424/183 X |
| 3,794,584 | 2/1974 | Kunin | 128/214 R X |
| 3,799,355 | 3/1974 | Salyer et al. | 210/500 M |
| 3,799,356 | 3/1974 | Salyer et al. | 210/500 M |
| 3,865,726 | 2/1975 | Chibata et al. | 210/321 B X |
| 3,874,907 | 4/1975 | Gardon et al. | 210/321 B X |

FOREIGN PATENT DOCUMENTS 2,435,702  2/1975  Germany .......................... 210/321 B

OTHER PUBLICATIONS

Techniques of Applying a Graphite-Benzalkonium--Heparin Coating to Various Plastics & Metals, Gott et al., 1964, vol. X, Trans. Amer. Soc. Artif. Int. Organs pp. 213-217.
Sanders, Artifical Organs, 4/5/71, Chemical and Engineering News, pp. 32-50.
Sanders, Artificial Organs, 4/12/71, Chemical and Engineering News, pp. 68-76.

Primary Examiner—Wilbur L. Bascomb, Jr.
Assistant Examiner—Robert H. Spitzer
Attorney, Agent, or Firm—Littlepage, Quaintance, Murphy, Richardson and Webner

[57] ABSTRACT

A biocompatible hemoperfusion system employing a polymer-coated detoxicant composition comprising a solid detoxicant having a semipermeable polymer coating which substantially retains free heparin is disclosed. The semipermeable polymer coating has an effective pore size permitting waste metabolites and toxins to diffuse therethrough. A cartridge for extracorporeal hemoperfusion comprising a plurality of particles is provided.

25 Claims, 3 Drawing Figures

BIOCOMPATIBLE HEMOPERFUSION SYSTEM

The concept of perfusing human blood through a column of detoxicant particles for the purpose of removing or modifying waste metabolites and toxic substances is well-known (Yatzidis, H. A convenient hemoperfusion micro-apparatus over charcoal. Proc. Europ. Dial. Transplant Ass., 1:83, 1964). While the technique is initially very effective, such previous attempts at hemoperfusion have been plagued by very high losses of white cells and platelets (Dunea, G. and Kolff, W. J. Clinical experience with the Yatzidis charcoal artificial kidney. Trans. Amer. Soc. Artif. Int. Organs, 11:179, 1965), as well as clotting, sludging, and channeling of blood in the column. The column then becomes ineffective and the patient suffers thromobocytopenia. Further, fine detoxicant particles tend to be released into the blood stream to become emboli in blood vessels and organs such as the lungs, spleen, and kidneys (Hagstam, K. E., Larsson, L. E., and Thysell, H. Experimental studies on charcoal hemoperfusion in phenobarbital intoxication and uremia including histological findings. Acta. Med. Scand., 180:593, 1966).

Platelet loss and detoxicant emboli present such serious hazards to the patient that hemoperfusion has heretofore received only very limited experimental use. With these problems overcome, hemoperfusion offers an extremely valuable method of quickly removing harmful substances from the blood, many of which can be removed or made harmless by no other means.

T. M. S. Chang in U.S. Pat. No. 3,522,346 has suggested applying a thin semi-permeable collodion membrane containing a quarternary ammonium heparin-complex to the surface of the detoxicant particles in order to encapsulate the particles and render them non-thrombogenic. However, because of the markedly reduced activity and effectiveness of complexed heparin, Chang subsequently discovered that a very large quantity of this heparin-complex is required for non-thrombogenicity, which necessitates a very thick membrane to contain the complex. Chang reported that this thick membrane inhibits toxin removal and thereby renders the whole process ineffective (T. M. S. Chang, Artificial Cells, pg. 136, C. C. Thomas, 1972). The use of a larger quantity of the heparin-complex also tends to lyse erythrocytes (Artificial Cells, pg. 118). If the fragile membrane is damaged or has a defect, clotting will occur (Artificial Cells, pg. 121).

Chang has since abandoned the heparin-complex approach in favor of detoxicants coated with a membrane of collodion and a second coating of non-thrombogenic albumin (Chang, U.S. Pat. No. 3,725,113, hereafter Chang 113). However, albumin is very costly, and because it cannot be completely sterilized, it carries the threat of hepatitis. This warning is usually stated on the container label. After application of the albumin, the coated particles must be kept under refrigeration at 4° C. for 15 hours (Chang 113, Col. 3, line 30), and then generally used within 24 hours (Chang 113, line 32). Because the albumin coating is quite susceptible to biological degradation, the coated particles cannot be prepared far in advance or easily stored. The coated particles must not contact air at any time (Artifical Cells, pg. 138).

A soluble albumin must completely coat every particle, but the albumin coating is subject to exchange phenomena (J. L. Brash, et. al., Exchange of Albumin Adsorbed on Polymer Surfaces, Trans. Amer. Soc. Artif. Int. Organs, 20:69, 1974), and may be removed, rapidly exchanged, or reduced by equilibration with a low albumin blood level, which is quite common with many hepatic disorders, for example. With exchange or reduction of the albumin coating, clotting can begin, and platelets can adhere to the collodion coating.

It is therefore an object of the present invention to provide an improved biocompatible hemoperfusion system substantially free of one or more of the disadvantages of prior systems. Another object is to provide a polymercoated detoxicant composition which does not result in an undesirable reduction in the platelet and leucocyte level in the blood.

A further object is to provide an improved polymer-coated detoxicant composition which is effective in the removal of waste metabolites and toxins.

A still further object of the present invention is to provide an improved polymer-coated detoxicant composition which prohibits the escape of emboli.

Yet another object of the present invention is to provide an improved polymer coated detoxicant composition which is truly non-thrombogenic.

Still another object is to provide an improved process for cleaning the detoxicant composition.

Still another object is to provide an improved cartridge for extracorporeal hemoperfusion which is easily handled, stored and sterilized.

Still another object is to provide an improved process for extracorporeal hemoperfusion.

Additional objects and advantages of the present invention will be apparent to those skilled in the art by reference to the detailed description and drawings wherein.

Figure 1:
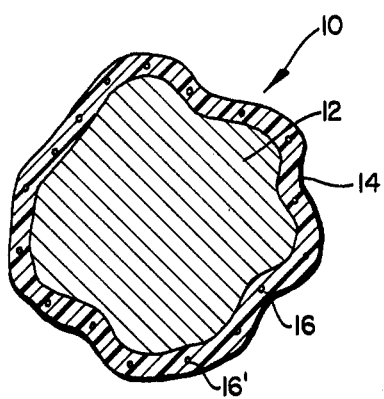
FIG. 1 is a greatly enlarged view of a particle of the detoxicant composition of the present invention.

According to the present invention there is provided a polymer coated detoxicant composition adapted for reaction in an extracorporeal shunt with waste metabolites and toxins found in blood comprising a solid detoxicant having a semipermeable polymer coating: having an effective pore size permitting waste metabolites and toxins to diffuse therethrough; having free heparin therein; having an effective pore size permitting substantial retention of the free heparin by the polymer coating; being insoluble in blood.

According to the present invention the solid detoxicant can be any solid detoxicant which can be polymer coated, such as those heretofore employed in extracorporeal hemoperfusion. Examples of suitable solid detoxicants include among others, ion exchange resins, activated carbon, enzymes, enzyme adducts, chromatograph gels, and assorted polymer absorbents. Activated carbon, particularly activated carbon of petroleum origin is a preferred solid detoxicant because of cost, availability, activity, strength, attrition resistance, and a broad removal spectrum.

The solid detoxicant is coated with a semipermeable polymer. The polymer coating has an effective pore size permitting waste metabolites and toxins to diffuse therethrough. The effective pore radii of the polymer coating may be varied over a wide range, but is generally within the range of 1 to 30 A with the preferred average effective pore radii between 3 and 15 A. Pore radii appreciably smaller than 1 A are impermeable to electrolytes; pore radii appreciably larger than 30 A have reduced selectivity. However, the pore size is such that the free heparin is substantially retained by the polymer membrane. In a preferred embodiment the calculated average pore radius is 4 A; this pore size substantially retains free heparin which has a characteristic radius of 15 A. Free heparin so retained has a powerful antithrombogenic effect. It interrupts the clotting mechanism and prevents aggregation of platelets on the surface of the detoxicant composition. Free heparin is any form of heparin which is soluble in blood, such as sodium heparin, U. S. P. (known variously as heparin sodium or sodium heparinate), as well as synthetic heparin (heparinoids).

The pore size of the polymer may be varied over a wide range and still effect substantial retention of the free heparin. Absolute retention of the free heparin is not required, so long as the migration and loss of the free heparin through the polymer coating is sufficiently slow that the detoxicant composition has time to selectively acquire a non-thrombogenic plasma protein coating during hemoperfusion. Such slowlyleached free heparin tends to remain localized and serves to impart thromboresistance to neighboring areas which may have been incompletely coated or damaged by mechanical abuse; the detoxicant composition does not have to be perfectly encapsulated in order to retain thromboresistance and therefore may be easily shipped, stored, and handled.

Preferably, the free heparin may be added to the polymer prior to coating the polymer on to the solid detoxicant. Alternatively, the free heparin may be first sorbed on to the solid detoxicant and the polymer subsequently applied, or the polymer may be coated on to the solid detoxicant and the heparin subsequently applied; in either case the heparin will migrate into the polymer. In any of these processes, the pore size of the polymer coating is effective for substantial retention of the free heparin. Heparin complexes are unsuitable for use in the present invention because they are insoluble in blood; they are insufficiently non-thrombogenic; they can lyse erythrocytes.

A wide variety of polymers can be employed in the present invention as long as they are insoluble in blood, non-toxic, non-pyrogenic, and sterilizable, and as long as they meet the other criteria specified herein. The pore size of the polymer coatings can be varied by techniques well known to those skilled in the art which techniques alone form no part of the present invention. Thus, it is well known to vary the pore size of a given polymer coating by varying the amount of cross-linking in the polymer or treating the polymer with various solutes. The polymer must be insoluble in blood in order to ensure association of the free heparin with the solid detoxicant. Albumin is blood soluble and is not a suitable polymer for use in the present invention.

Polymers useful in the present invention include, among others collodion (cellulose nitrate), cellulose acetate, deacetylated cellulose acetate, hydroxyethylcellulose, and hydrogels such as those of the acrylic series. Examples of suitable acrylic hydrogels include, among others, polymers of propylene glycol monoacrylate, glyceryl methacrylate, polyhydroxyethylacrylate, polyhydroxymethylacrylate, and most preferably polyhydroxyethylmethacrylate and polyacrylamide, as well as copolymers and grafts, such as copoly(acrylamidehydroxyethylmethacrylate).

Hydrogels are three-dimensional hydrophilic polymer networks capable of imbibing large quantities of water without dissolution of the polymer network. The water thus contained in a hydrogel greatly reduces the interfacial free energy between the blood and the hydrogel, and therefore greatly reduces the tendency of the elements of blood to adhere to the surface. When a hydrogel is used to substantially retain free heparin, the combined effects provide an extremely thromboresistant surface with efficient molecular transport which allows the use of heavier coatings for additional strength. Polyhydroxyethylmethacrylate is particularly well-suited for this invention because it has excellent heat resistance and it is well-characterized biochemically.

The weight of the polymer coating on the solid detoxicant may be varied over a wide range, but generally increases the weight of the solid detoxicant from .1% to 50% and preferably from .3% to 30%. Extremely light coatings are fragile; very heavy coatings retard diffusion.

The amount of heparin substantially retained by the polymer may be varied over a very wide range, but is generally from 500 to 25,000 units heparin per 100 gram detoxicant and is preferably approximately 5000 units of heparin per 100 grams of relatively coarse detoxicant, coated with a polymer which allows only slow migration of the heparin.

The coated detoxicant particles may be safely contained after the coating procedure by transferring them to a filter cartridge which keeps the particles under constant physical compression so that relative motion between the particles and the consequent generation of emboli are prevented when the particles are perfused. The compression tends to nullify opposing stresses which the detoxicant particles are less well able to withstand.

There are several means of achieving this movement - inhibiting compression. For example, the column of detoxicant particles may be fitted with a spring-loaded filter screen at either or both ends. Similarly, fixed screens could be used, and the body of particles surrounded by a spring-loaded collar. While such arrangements are effective, however, they are not readily adaptable to a wide variety of column designs.

A much more satisfactory, convenient, and adaptable method is the preferred embodiment of containing the body of particles under movement - inhibiting compression within a woven or knitted mesh sack which has elastic properties. A knitted mesh tube of four strand, crimped filament nylon, for example, has been used.

Immediately prior to use, the filled elastic mesh cartridge should be perfused with a biocompatible washing perfusate at a flow rate higher than the anticipated hemoperfusion rate in order to thoroughly wash the cartridge until the effluent is free of any particulates. Perfusion at this high flow rate subjects the detoxicant particles to higher stresses than will be encountered during hemoperfusion and assures that any possible fragments will be harmlessly released prior to connection to the patient.

Broadly speaking, any higher flow rate is suitable, however, the flow rate is at least five percent and preferably at least 20 percent greater than the hemoperfusion flow rate. Any biocompatible perfusate previously employed for similar processes can be employed in the process of the present invention. Non-limiting examples of suitable biocompatible washing perfusates include, among others, normal saline solution with 2000 units per liter of sodium heparin, Ringer's lactate with 1000 units per liter of sodium heparin and dextrose 5%. The blood can be passed through the detoxicant composition at rates varying between 10 to 600 ml/min.

Referring now to the drawings and in particular to FIG. 1, there is shown a detoxicant particle 10 that can be a member of the group of particles making up the polymer coated detoxicant composition of the present invention. The detoxicant particle 10 comprises a solid detoxicant 12 and a semipermeable polymer coating 14. The polymer coating 14 contains free heparin shown schematically as the dots 16, 16'. The polymer coating 14 has pores (not shown) whose effective pore size permits waste metabolites and toxins to diffuse through the polymer coating 14 and contact the solid detoxicant 12. However, the pore size permits substantial retention of the free heparin shown as dots 16, 16' by the polymer coating 14.

Figure 2:
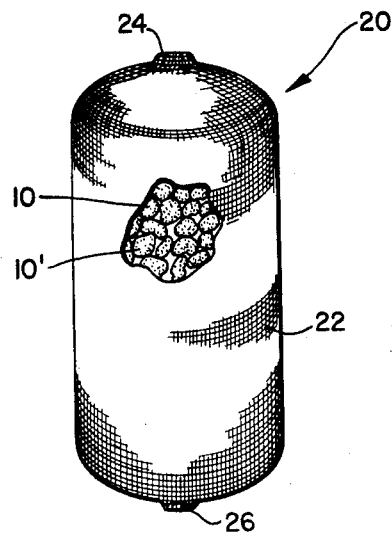
FIG. 2 is a partially cut away view of a cartridge of the present invention useful in extracorporeal hemoperfusion.

Referring now to FIG. 2, there is shown a cartridge 20 useful for extracorporeal hemoperfusion. The cartridge 20 comprises a plurality of particles 10, 10' held under movement inhibiting compression within a tube 22. The tube 22 can be of any blood compatible material which can be used in an elastic configuration but in a preferred embodiment is knitted of crimped nylon filament. The tube 22 is closed at its upper end 24 and at its lower end 26. The opening in the mesh are larger than blood cells but are smaller than the particles 10, 10'. The tube 22 is outwardly stretched in all directions and is in contact with the particles of solid detoxicant. The tube 22 holds the particles of solid detoxicant under movement inhibiting compression which reduces the tendency of the particles to fracture. In the embodiment shown in FIG. 2 optimum results are achieved by employing the polymer-coated detoxicant particles 10, 10' of the present invention. For example, a hydrogel swells as it is hydrated, thus further stretching the tube 22 and increasing the compression. However, the advantages of the absence of embolism causing particles achieved by the use of a tube 22 can be employed with particles other than the polymer-coated particles 10, 10' of the present invention.

Figure 3:
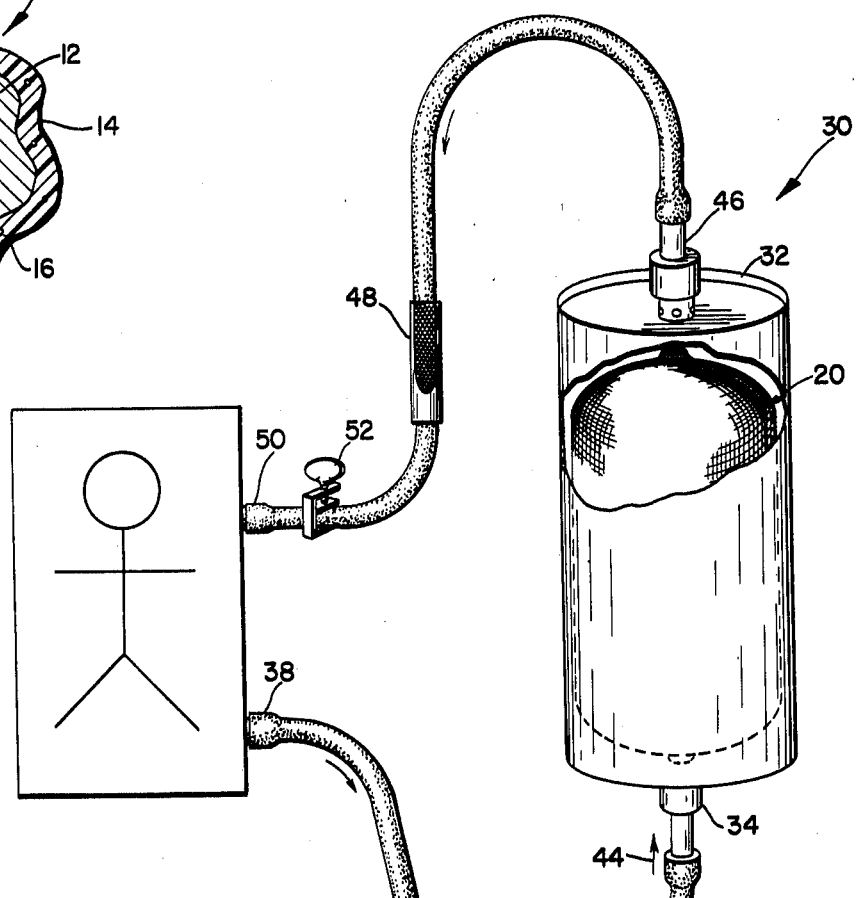
FIG. 3 is a schematic representation of the hemoperfusion system of the present invention.

Referring now to FIG. 3, there is shown a biocompatible hemoperfusion system 30 of the present invention. As shown in FIG. 3 a cartridge 20 is loaded into a suitable hemoperfusion chamber 32. An inlet port 34 is connected via tubing 36 to the patient's arterial access either directly or through a peristaltic blood pump 40 adapted to rotate in the direction of the arrow 42 causing blood to flow through the system 30 in the direction of the arrow 44. An outlet port 46 is connected through a combined bubble trap-filter 48 to the patient's venous access 50. Blood height in the bubble trap-filter 48 is controlled by a clamp 52. The outlet port 46 is designed so that it cannot be easily occluded. The chamber 32 is capable of withstanding pressure so that it can be used in conjunction with hemodialysis. Manometers may be inserted to monitor inlet and outlet pressures.

The invention may be better understood by reference to the following examples wherein all parts and percentages are by weight unless otherwise indicated. These examples are designed to teach those skilled in the art how to practice the present invention and represent the best mode presently contemplated for carrying out the present invention.

Many variations within the scope of this invention will be apparent to those skilled in the art. All reagents, solvents, initiators, and the like should be selected for the greatest blood compatibility and the lowest ultimate toxicity.

EXAMPLE 1

This example shows the synthesis of a polymer coated detoxicant composition of the present invention employing a preferred polymer.

The following quantities of the following ingredients are combined as indicated.

| Item | Ingredient | Quantity | |
|---|---|---|---|
| A | monomer solution of ethylene glycol monomethacrylate containing 1.5 ethylene glycol dimethacrylate | 22.5 | ml |
| B | | — | |
| C | ethanol (95%) | 225 | ml |
| D | sodium heparin (10,000 units/ml) | 1 | ml |
| E | ammonium persulfate (6%) | .75 | ml |
| F | sodium metabisulfite (12%) | .75 | ml |
| G | activated carbon particles | 225 | grams |

Items A and B are added to a vessel containing Item C. Item D is then added to the vessel with constant stirring. Items E and F are then added to the vessel. Item G is immediately dipped into the vessel until the evolution of heat ceases. The particles are then drained very briefly to remove gross fluid and spread on a tray to dry in an oven at 200° F. for 30 minutes. Higher temperatures can be employed but very fast drying encourages undesirable fracture. The particles are then stored dry. They may be steam sterilized at 250° F. for 30 minutes.

EXAMPLE 2

This example illustrates the synthesis of a polymer coated detoxicant composition of the present invention employing another preferred polymer.

The following quantities of the following ingredients are combined as indicated.

| Item | Ingredient | Quantity | |
|---|---|---|---|
| A | acrylamide | 22.5 | grams |
| B | methylenebisacrylamide | 2.5 | grams |
| C | dimethylaminopropionitrile | 1 | ml |
| D | ammonium persulfate | 1.25 | grams |
| E | sodium heparin (10,000 units/ml.) | 1 | ml |
| F | pyrogen - free distilled water to final volume of | 250 | ml |
| G | activated carbon (12 × 30 mesh) | 225 | grams |

Items A and B are dissolved in 200 ml of Item F which is contained in a vessel. Items C, D and E are added with constant stirring. Item F then added with stirring until the final solutions volume is 250 ml. Item G is immediately dipped into the vessel until the evolution of heat ceases. The particles are then drained very briefly to remove gross fluid and spray on a tray. They are then placed in an oven at 200° F. until sufficiently dry for convenient storage. They may be steam sterilized at 250° F. for 30 minutes.

EXAMPLE 3

This example illustrates the synthesis of a polymer-coated detoxicant composition of the present invention employing collodion as the polymer.

The following quantities of the following ingredients are combined as indicated.

| Item | Ingredient | Quantity | |
|------|-----------|---------|---|
| A | Collodion, U. S. P. | 30 | ml. |
| B | Acetone | 219 | ml. |
| C | Sodium Heparin (10,000 units/ml.) | 1 | ml. |
| D | Activated Carbon (12 × 30 mesh) | 225 | grams |

Item A is added to a vessel containing Item B. When Item A has dissolved, Item C is added with constant stirring. Item D is then immediately dipped into the vessel until the evolution of heat ceases. The particles are then briefly drained and spread on a tray to dry under low heat (120° F.) until of constant weight. The particles may be stored dry. They may be steam sterilized at 250° F. for 30 minutes.

EXAMPLE 4

This example illustrates the synthesis of a polymer-coated detoxicant composition of the present invention wherein the polymer is cellulose acetate.

The following quantities of the following ingredients are combined as indicated.

| Item | Ingredient | Quantity | |
|------|-----------|---------|---|
| A | Cellulose acetate (approx. 40% acetyl) | 1 | grams |
| B | Acetone to final volume of | 250 | ml. |
| C | Sodium heparin (10,000 units/ml) | 1 | ml. |
| D | Activated carbon (12 × 30 mesh) | 225 | grams |

Item A is placed in a vessel and 200 ml of Item B is added with stirring. When Item A has dissolved, Item C is added with stirring. Item B is then added to bring the final volume to 250 ml. Item D is then immediately dipped into the vessel until the evolution of heat ceases. The particles are then briefly drained and spread on a tray to dry under low heat (120° F.) until of constant weight. The particles may be stored dry. They may be steam sterilized at 250° F. for 30 minutes.

EXAMPLE 5

This example illustrates the synthesis of a polymer-coated detoxicant composition of the present invention wherein the free heparin is sorbed on the carbon particles.

The following quantities and the following ingredients are combined as indicated.

| Item | Ingredient | Quantity | |
|------|-----------|---------|---|
| A | Sodium heparin (10,000 units/ml) | 1 | ml |
| B | Pyrogen - free distilled water | 249 | ml |
| C | Activated carbon | 225 | grams |

Item A is added with stirring to a vessel containing Item B. Item C is then dipped into the vessel until most of the fluid is absorbed. The particles are spread on a tray to dry in an oven at 200° F. until of constant weight. These particles may be used for the activated carbon particles in any of the previous examples. The particles may be similarly coated with any of the polymers except that heparin is not included in the coating solutions. Ethyl alcohol may be added to Item B to hasten drying.

EXAMPLE 6

This example illustrates the production of a cartridge similar to the cartridge 20 of FIG. 2.

A circular knit tube of four-strand, crimped filament, stretch nylon with approximate relaxed dimensions of width 2 inches and length 5 inches is sewn or tied closed at one end. From the opposite end, the tube is loaded with detoxicant particles and stretched until its taut dimensions are approximately 2.25 inches O. D. by 7.5 inches long. The other end is then sewn closed or tied off. When stretched taut, the great interstices average 60 mesh per inch.

EXAMPLE 7

This example illustrates a clinical trial of the polymer coated detoxicant composition of the present invention.

This 50 year old white female was admitted to the intensive care unit in a rapidly - deepening, stage 4 hepatic coma. Physical examination revealed acute distress with doll's eye movements and dilated pupils poorly responsive to light. Bleeding was present from exophageal varices. Because of respiratory distress, she was intubated and placed on a volume respirator. A Sengstaken - Blakemore tube was placed to control the bleeding. Laboratory findings were abnormal, including low blood count (platelets 105,000/mm$^3$). EEG revealed generalized slowing with acute electrical dysfunction consistent with metabolic abnormality; the tri-phasic pattern typical of hepatic coma was present. The impression was Laennec's Cirrhosis; the coma was unresponsive to intensive treatment with classical measures.

It was decided to attempt hemoperfusion in order to obviate the comma and improve the patient's condition. The patient was cannulated with femoral vein catheters using the Seldinger technique.

Prior to hemoperfusion, the cartridge (Examples 1 and 6) was perfused with 2 liters of heparinized normal saline (2,000 units sodium heparin injection/liter) at a flow rate of 300 ml/minute. The patient was connected to the apparatus and perfused for 2 hours at a flow rate of 150 ml/minute under regional heparinization. During this first hemoperfusion, an EEG was conducted and showed gradual, definite improvement, with reduction of the tri-phasic pattern. Platelet loss through the cartridge was insignificant (post-perfusion platelets were 94,000 mm$^3$).

Three subsequent hemoperfusions were conducted, once each following day. Each hemoperfusion lasted 2 hours, following the above procedure.

After the third hemoperfusion, the patient showed some awakening; she was responsive to her name and had spontaneous movements of the extremities.

After the fourth hemoperfusion, the patient awoke. She became alert, talking, and oriented. Tubes were removed.

The patient was subsequently treated with full supportive measures for a few weeks in the hospital, was ultimately discharged to outpatient followup, and has continued excellent recovery.

There were no adverse reactions to any of the hemoperfusions. No blood clots were found in the cartridges; there was no evidence of particle emboli; and platelet loss was negligible. No loss of these properties and no adverse reactions have occurred in human clinical trials of more than 50 similar hemoperfusions with this biocompatible hemoperfusion system. The cartridges have been stored, handled, and used in standard hospital setting.

Although the invention has been described in considerable detail with reference to certain preferred embodiments thereof, it will be understood that variations and modifications can be effected within the spirit and scope of the invention as described above and as defined in the appended claims.

What is claimed is:

1. A polymer-coated detoxicant composition adapted for reaction in an extracorporeal shunt with waste metabolites and toxins found in blood comprising a solid detoxicant having a semipermeable polymer coating: having an effective coating pore size permitting waste metabolites and toxins to diffuse therethrough; having free heparin therein; having an effective coating pore size permitting substantial retention of the free heparin by the polymer membrane; being insoluble in blood.

2. The detoxicant composition of claim 1 wherein the solid detoxicant is activated carbon.

3. The detoxicant composition of claim 1 wherein the polymer is a hydrogel.

4. The detoxicant composition of claim 1 wherein the polymer is cross-linked.

5. The detoxicant composition of claim 1 wherein the polymer is collodion.

6. The detoxicant composition of claim 1 wherein the polymer is cellulose acetate.

7. The detoxicant composition of claim 1 wherein the polymer is polyacrylamide.

8. The detoxicant composition of claim 1 wherein the polymer is polyhydroxyethylmethacrylate.

9. The detoxicant composition of claim 1 wherein the pores have an effective radii of 1 to 30 A.

10. The detoxicant composition of claim 1 wherein the weight of the polymer coating to the solid detoxicant is from 0.1% to 50%.

11. The detoxicant composition of claim 1 wherein the amount of heparin substantially retained by the polymer coating is approximately 5000 units per 100 grams of detoxicant.

12. A process for extracorporeal hemoperfusion comprising the step of passing the blood through a polymer-coated detoxicant composition adapted for reaction in an extracorporeal shunt with waste metabolites and toxins found in blood and which composition comprises a solid detoxicant having a semipermeable polymer coating: having an effective coating pore size permitting waste metabolites and toxins to diffuse therethrough; having free heparin therein; having an effective coating pore size permitting substantial retention of the free heparin by the polymer coating; being insoluble in blood.

13. The process of claim 12 wherein the blood is passed through the detoxicant composition at a rate of 10 to 600 ml/min.

14. A process for extracorporeal hemoperfusion comprising the step of passing blood through a detoxicant composition of particles having a semipermeable polymer coating: having an effective coating pore size permitting waste metabolites and toxins to diffuse therethrough; having free heparin therein; having an effective coating pore size permitting substantial retention of the free heparin by the polymer membrane; being insoluble in blood, the particles of which are maintained under movement-inhibiting compression.

15. The process of claim 14 wherein the movement-inhibiting compression is omnidirectional.

16. The process of claim 14 wherein the movement-inhibiting compression is directed radially inwardly with respect to the mass of the detoxicant composition.

17. The process of claim 14 wherein the movement-inhibiting compression is sufficient to eliminate completely movement of one particle of the composition with respect to other particles of the composition.

18. A cartridge for extracorporeal hemoperfusion comprising a plurality of particles of solid detoxicant having a semipermeable polymer coating: having an effective coating pore size permitting waste metabolites and toxins to diffuse therethrough; having free heparin therein; having an effective coating pore size permitting substantial retention of the free heparin by the polymer membrane; being insoluble in blood held under movement-inhibiting compression within a blood-permeable container.

19. A cartridge for extracorporeal hemoperfusion comprising:
A. a plurality of particles of solid detoxicant having a semipermeable polymer coating: having an effective coating pore size permitting waste metabolites and toxins to diffuse therethrough; having free heparin therein; having an effective coating pore size permitting substantial retention of the free heparin by the polymer membrane; being insoluble in blood held under movement inhibiting compression within:
B. a knitted nylon mesh tube surrounding the particles wherein:
  1. the tube is closed at its upper and lower ends;
  2. the openings in the mesh are larger than blood cells but smaller than the particles of solid detoxicant;
  3. the tube is outwardly stretched in all directions and is in contact with the particles of solid detoxicant holding them under movement-inhibiting compression.

20. A process for extracorporeal hemoperfusion comprising the step of passing the blood through a cartridge comprising:
A. a plurality of particles of solid detoxicant composition comprising a solid detoxicant having a semipermeable polymer coating: having an effective pore size permitting waste metabolites and toxins to diffuse therethrough; having free heparin therein; having an effective pore size permitting substantial retention of the free heparin by the polymer coating; being insoluble in blood, and said solid detoxicant composition is held under movement inhibiting compression within:
B. a knitted nylon mesh tube surrounding the particles wherein:
  1. the tube is closed at its upper and lower ends;
  2. the openings in the mesh are larger than blood cells but smaller than the particles of solid detoxicant;
  3. the tube is outwardly stretched in all directions and is in contact with the particles of solid detoxicant holding them under movement-inhibiting compression.

21. A process of claim 20 wherein prior to hemoperfusion the cartridge is perfused with a biocompatible washing perfusate at a flow rate higher than the hemoperfusion rate.

22. A process of claim 21 wherein the washing flow rate is at least 5% greater than the hemoperfusion rate.

23. A process of claim 21 wherein the washing flow rate is at least 20% greater than the hemoperfusion rate.

24. A process for extracorporeal hemoperfusion comprising sequentially:

I. perfusing a cartridge containing particulate detoxicant composition with a biocompatible washing perfusate, II. and then passing blood through the cartridge at a rate less than the rate at which the biocompatible washing perfusate is perfused through the cartridge.

25. A process for extracorporeal hemoperfusion comprising sequentially:

I. Perfusing a cartridge containing particulate detoxicant composition wherein the cartridge comprises:
  A. a plurality of particles of solid detoxicant held under movement inhibiting compression within:
  B. a knitted nylon mesh tube surrounding the particles wherein:
    1. the tube is closed at its upper and lower ends;
    2. the openings in the mesh are larger than blood cells but smaller than the particles of solid detoxicant;
    3. the tube is outwardly stretched in all directions and is in contact with the particles of solid detoxicant holding them under movement-inhibiting compression, and wherein the particulate detoxicant composition comprises a solid detoxicant having a semi-permeable polymer coating, having an effective coating pore size permitting waste metabolities and toxins to diffuse therethrough; having free heparin therein; having an effective coating pore size permitting retention of the free heparin by the polymer membrane; being insoluble in blood;

II. and then passing blood through the cartridge at a rate less than the rate at which the biocompatible washing perfusate is perfused through the cartridge.

* * * * *